(12) United States Patent
Huang et al.

(10) Patent No.: US 12,390,163 B2
(45) Date of Patent: Aug. 19, 2025

(54) COMPOSITE MICRONEEDLE STRUCTURE BASED ON INTEGRATED CIRCUIT CHIP

(71) Applicant: WUHAN NEURACOM TECHNOLOGY DEVELOPMENT CO., LTD., Wuhan (CN)

(72) Inventors: Li Huang, Wuhan (CN); Cheng Huang, Wuhan (CN); Bei Tong, Wuhan (CN)

(73) Assignee: WUHAN NEURACOM TECHNOLOGY DEVELOPMENT CO., LTD., Wuhan (CN)

( * ) Notice: Subject to any disclaimer, the term of this patent is extended or adjusted under 35 U.S.C. 154(b) by 0 days.

(21) Appl. No.: 18/964,008

(22) Filed: Nov. 29, 2024

(65) Prior Publication Data

US 2025/0090097 A1 Mar. 20, 2025

Related U.S. Application Data

(63) Continuation of application No. PCT/CN2022/127285, filed on Oct. 25, 2022.

(30) Foreign Application Priority Data

Aug. 24, 2022 (CN) .......................... 202211015746.0

(51) Int. Cl.
*A61B 5/00* (2006.01)
*A61B 5/293* (2021.01)

(52) U.S. Cl.
CPC .............. *A61B 5/685* (2013.01); *A61B 5/293* (2021.01); *A61B 2562/125* (2013.01)

(58) Field of Classification Search
CPC ... A61B 5/685; A61B 5/293; A61B 2562/125; A61N 1/00
See application file for complete search history.

(56) References Cited

U.S. PATENT DOCUMENTS 11,166,782 B1 11/2021 Schermers et al.
2010/0331935 A1* 12/2010 Tabada ..................... A61N 1/05
600/377

(Continued)

FOREIGN PATENT DOCUMENTS

CN 101884530 A 11/2010
CN 102686147 A 9/2012
(Continued)

OTHER PUBLICATIONS

First Office Action issued in counterpart Chinese Patent Application No. 202211015746.0, dated Nov. 2, 2023.
(Continued)

*Primary Examiner* — Adam Z Minchella
(74) *Attorney, Agent, or Firm* — Westbridge IP LLC

(57) ABSTRACT

A composite microneedle structure based on an integrated circuit chip includes a microstrip line, at least one microprobe and at least one integrated circuit chip. The microprobe includes a hard needle and a soft needle, the soft needle is fixed to an upper surface of the hard needle by a fixed structural member, and the integrated circuit chip is provided at a tail of the microprobe; the integrated circuit chip and the soft needle of the microprobe are fixed to form an electrical connection, and the microstrip line and one end of the integrated circuit chip are fixed to form the electrical connection.

7 Claims, 9 Drawing Sheets

(56) References Cited

U.S. PATENT DOCUMENTS

| | | | | |
|---|---|---|---|---|
| 2013/0131482 | A1* | 5/2013 | Fedder | A61B 5/291 264/494 |
| 2014/0378993 | A1* | 12/2014 | Shah | A61N 1/05 428/172 |
| 2015/0157862 | A1 | 6/2015 | Greenberg et al. | |
| 2018/0353750 | A1* | 12/2018 | Hetke | A61N 1/05 |
| 2022/0143418 | A1 | 5/2022 | Cortese et al. | |

FOREIGN PATENT DOCUMENTS

| | | | |
|---|---|---|---|
| CN | 109171718 | A | 1/2019 |
| CN | 114209332 | A | 3/2022 |
| CN | 114209333 | A | 3/2022 |
| CN | 114305432 | A | 4/2022 |
| CN | 114305433 | A | 4/2022 |
| CN | 114343654 | A | 4/2022 |
| CN | 114469117 | A | 5/2022 |
| CN | 114699087 | A | 7/2022 |
| CN | 114788700 | A | 7/2022 |
| CN | 114847957 | A | 8/2022 |
| CN | 115227254 | A | 10/2022 |
| CN | 115500832 | A | 12/2022 |
| WO | 2013131261 | A1 | 9/2013 |

OTHER PUBLICATIONS

International Search Report and Written Opinion issued in corresponding PCT Application No. PCT/CN2022/127285, dated Mar. 20, 2023.

Notification to Grant Patent Right for Invention issued in counterpart Chinese Patent Application No. 202211015746.0, dated Dec. 16, 2023.

* cited by examiner

COMPOSITE MICRONEEDLE STRUCTURE BASED ON INTEGRATED CIRCUIT CHIP

CROSS-REFERENCE TO RELATED APPLICATIONS

This application is a continuation application of International Application No. PCT/CN2022/127285, filed on Oct. 25, 2022, which claims priority to Chinese Patent Application No. 202211015746.0, filed on Aug. 24, 2022. The disclosures of the above-mentioned applications are incorporated herein by reference in their entireties.

TECHNICAL FIELD

The present application belongs to the technical field of brain-computer interface neural microelectrode, and specifically relates to a composite microneedle structure based on an integrated circuit chip.

BACKGROUND

In the neural interface, brain signals are collected by electrodes. The electrodes include invasive form and non-invasive form. The brain signals collected by invasive electrodes are more accurate and reliable. At present, most invasive microneedle structures are single-type electrodes, such as Michigan electrodes and Utah electrodes with hard needle structures, and polyimide electrodes with soft needle structures. However, the hard needle (rigid needle) cannot be adaptively deformed with the expansion and contraction of the blood vessels during implantation, which may cause certain damage to the tissue. The soft needle structure is prone to deformation during implantation and requires the assistance of external equipment for implantation, which has problems such as complex structure and low efficiency. In addition, the functions of hard needles or soft needles are relatively simple, that is, they only have recording functions and do not have stimulation effects; more importantly, the Electroencephalogram signal has small amplitude, a low frequency range and is easily interfered by noise, and the current technology is not accurate enough in extracting Electroencephalogram signals.

SUMMARY

The purpose of the present application is to provide a composite microneedle structure based on an integrated circuit chip, which can at least solve some of the defects of the prior art.

To achieve the above-mentioned purpose, the present application adopts the following technical scheme:

A composite microneedle structure based on an integrated circuit chip, including a microstrip line, at least one microprobe and at least one integrated circuit chip; the microprobe includes a hard needle and a soft needle, the soft needle is fixed to an upper surface of the hard needle by a fixed structural member, and the integrated circuit chip is provided at a tail of the microprobe; the integrated circuit chip and the soft needle of the microprobe are fixed to form an electrical connection, and the microstrip line and one end of the integrated circuit chip are fixed to form the electrical connection.

Furthermore, the hard needle is provided with a hard needle tail and at least one hard needle microelectrode formed on the hard needle tail, and the soft needle is provided with a soft needle tail and at least one soft needle microelectrode formed on the soft needle tail; the soft needle tail is fixed to the hard needle tail, and the soft needle microelectrode is fixed to the hard needle microelectrode.

Furthermore, the fixed structural member includes a first fixing member for fixing the soft needle microelectrode and the hard needle microelectrode, and second fixing members for fixing the soft needle tail and the hard needle tail.

Furthermore, the first fixing member is a plurality of hook structures provided at intervals along a length direction of the hard needle microelectrode, the hook structure is provided with a first part and a second part, two ends of the second part are respectively connected to the first part and a surface of the hard needle microelectrode, and the first part is parallel to the surface of the hard needle microelectrode; the soft needle microelectrode is provided between the first part and the surface of the hard needle microelectrode, and the second part and the surface of the hard needle microelectrode are at a preset angle.

Furthermore, the preset angle between the second part of the hook structure and the surface of the hard needle microelectrode is an acute angle.

Furthermore, an opening for the hook structure to pass through is provided at a position corresponding to the hook structure on the soft needle microelectrode, and decoupling structures for the hook structure to detach from the soft needle is provided on the opening; the first part of the hook structure, the second part of the hook structure and the surface of the hard needle microelectrode form an open slot facing a needle tip of the hard needle, and the decoupling structure is provided at one end away from a needle tip of the soft needle.

Furthermore, the decoupling structure is decoupling parts extending from an edge of the opening into the opening, a spacing between the decoupling parts is smaller than a width of the second part of the hook structure, and the decoupling parts are symmetrically provided about an axis of the opening; a gap is provided between a side edge of the decoupling part and a side edge of a corresponding opening.

Furthermore, the second fixing members are a plurality of plug structures provided at intervals along a width direction of the hard needle at the hard needle tail, the plug structure includes two coaxial cylinders with a larger upper part and a smaller lower part, a plug hole is provided at the soft needle tail corresponding to the plug structure, and a plurality of central symmetrical figures are provided outward along an edge of the plug hole on the soft needle tail, and an upper cylinder diameter of the plug structure is larger than a diameter of the plug hole.

Furthermore, a connection between the soft needle tail and the integrated circuit chip is provided between the second fixing member and the soft needle microelectrode.

Furthermore, the integrated circuit chip includes a soft needle connecting section for connecting to the soft needle and a microstrip line connecting section for connecting to the microstrip line, and the microstrip line connecting section is provided at one side of the soft needle connecting section; the integrated circuit chip is electrically connected to the soft needle of the microprobe by face-down bonding, and the microstrip line is electrically connected to the integrated circuit chip by the face-down bonding.

Compared with the prior art, the present application has the following beneficial effects.

Firstly, the composite microneedle structure based on the integrated circuit chip provided by the present application, by directly integrating the microprobe with the integrated circuit chip, achieves the real-time, fast and accurate extraction and stimulation of neural signals to minimize transmission loss and reduce noise signals, thereby ensuring stable and lossless signal transmission.

Secondly, the composite microneedle structure based on the integrated circuit chip provided by the present application, by the design of bringing the soft needle into the tissue by the hard needle and then pulling out the hard needle, avoids the defects of using a single hard needle or a single soft needle.

Thirdly, the composite microneedle structure based on the integrated circuit chip provided by the present application, by patterning a decoupling structure on the soft needle microelectrode of the soft needle and growing a hook structure at the corresponding position of the hard needle, can drive the soft needle to be implanted by the hook structure on one hand, and can well fix the hard needle and the soft needle on the other hand, thus preventing the hard needle and the soft needle from moving, and reducing the risk of the soft needle warping at the same time.

Lastly, the composite microneedle structure based on the integrated circuit chip provided by the present application, by patterning the central symmetrical figure at the soft needle tail and growing the plug structure at the corresponding position of the hard needle, can well fix the hard needle and the soft needle, thus preventing them from moving, and ensuring the stability and accuracy of the soft needle implantation.

The present application will be further described in detail in conjunction with the accompanying drawings.

DETAILED DESCRIPTION OF THE EMBODIMENTS

The technical solutions in the embodiments according to the present application will be clearly and completely described below in conjunction with the accompanying drawings in the embodiments according to the present application, and it is clear that the described embodiments are only a part of the embodiments according to the present application, and not all of the embodiments. Based on the embodiments in the present application, all other embodiments obtained by those skilled in the art without making creative labor fall within the scope of the present application.

In the description of the present application, it should be understood that, the orientation or positional relationship indicated by the terms "center", "top", "bottom", "left", "right", "vertical", "horizontal", "inside", "outside", etc. is based on the orientation or positional relationship shown in the accompanying drawings, which are merely for convenience of describing the present application and simplifying the description, and do not indicate or imply that the devices or elements referred to must have a specific orientation or must be constructed and operate in a specific orientation, therefore, it cannot be construed as a limitation on the present application.

In the description of the present application, it should be noted that, unless otherwise clearly specified and limited, the terms "install", "join" and "connect" should be understood in a broad sense, for example, it can be a fixed connection, a detachable connection, a conflicting connection or an integral connection; for those skilled in the art, the specific meanings of the above terms in the present application can be understood according to specific circumstances.

The terms "first" and "second" are used for descriptive purposes only and should not be understood as indicating or implying relative importance or implicitly indicating the number of the indicated technical features. Therefore, the features defined as "first" and "second" may explicitly or implicitly include one or more of the features; in the description of the present application, unless otherwise specified, "a plurality of" means two or more.

Figure 1:
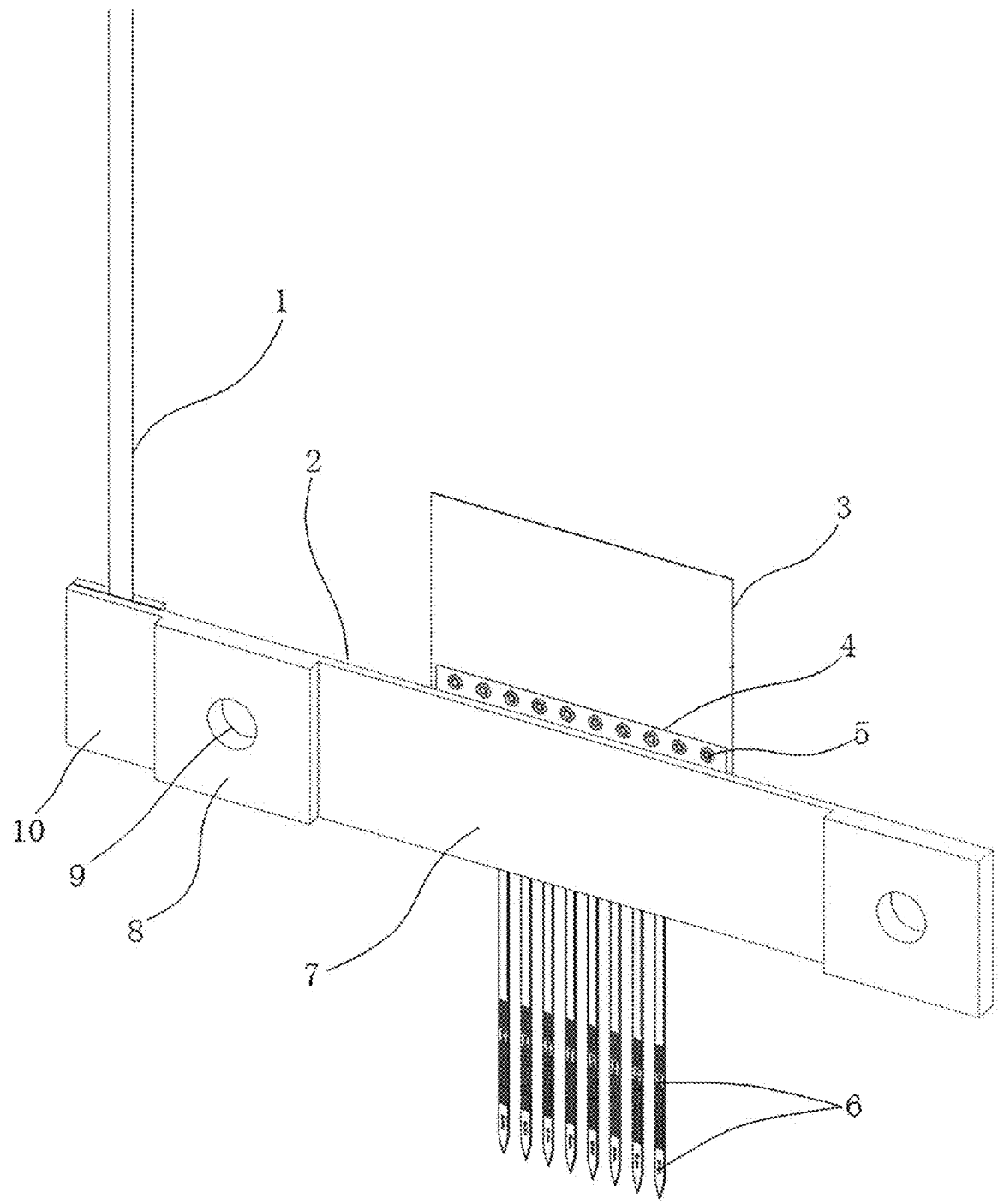
FIG. 1 is a schematic view of a composite microneedle structure based on an integrated circuit chip of the present application.
Figure 2:
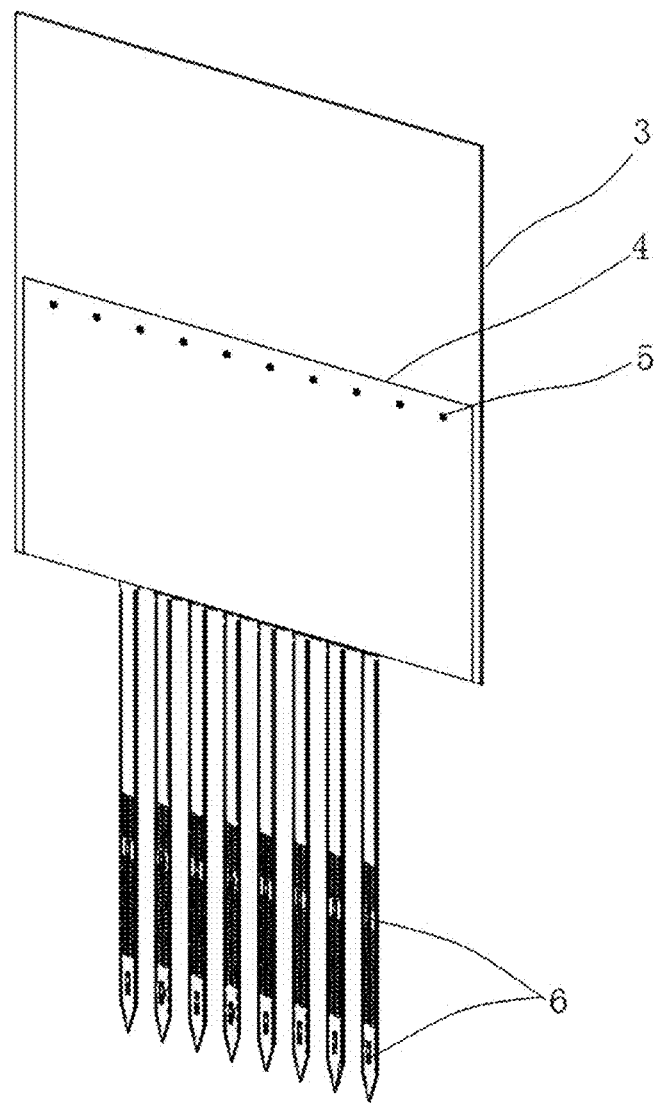
FIG. 2 is a structural schematic view of a microprobe in a composite microneedle structure of the present application.

As shown in FIG. 1 and FIG. 2, the embodiment provides a composite microneedle structure based on an integrated circuit chip including: a microstrip line 1, at least one microprobe and at least one integrated circuit chip 2. The microprobe includes a hard needle 3 and a soft needle 4, the soft needle 4 is fixed to an upper surface of the hard needle 3 by a fixed structural member, and the integrated circuit chip 2 is provided at a tail of the microprobe; the integrated circuit chip 2 and the soft needle 4 of the microprobe are fixed to form an electrical connection, and the microstrip line 1 and one end of the integrated circuit chip 2 are fixed to form the electrical connection. The hard needle 3 has certain rigidity and can be implanted into the soft tissue of the human body or the soft tissue of the animal. For example, the hard needle 3 can be made of silicon material. The soft needle 4 has certain flexibility. For example, the soft needle 4 can be made of silicon nitride, polycrystalline silicon, silicon carbide and other materials. In this embodiment, since the hard needle 3 has certain rigidity, the soft needle 4 is laid flat on the upper surface of the hard needle 3, so that the hard needle 3 can drive the soft needle 4 to be implanted into the soft tissue of the human body or the soft tissue of the animal. After the soft needle 4 is implanted into the tissue, the hard needle 3 is pulled out, the hard needle 3 is separated from the soft needle 4, and the soft needle 4 remains in the implanted tissue, thereby effectively avoiding the defects caused by using a single hard needle or soft needle. At the same time, the microprobe is integrated with the integrated circuit chip 2, which can realize the on-site collection and stimulation of neural signals, and accordingly optimize the functionality of the neural interface to better meet clinical needs.

Figure 3:
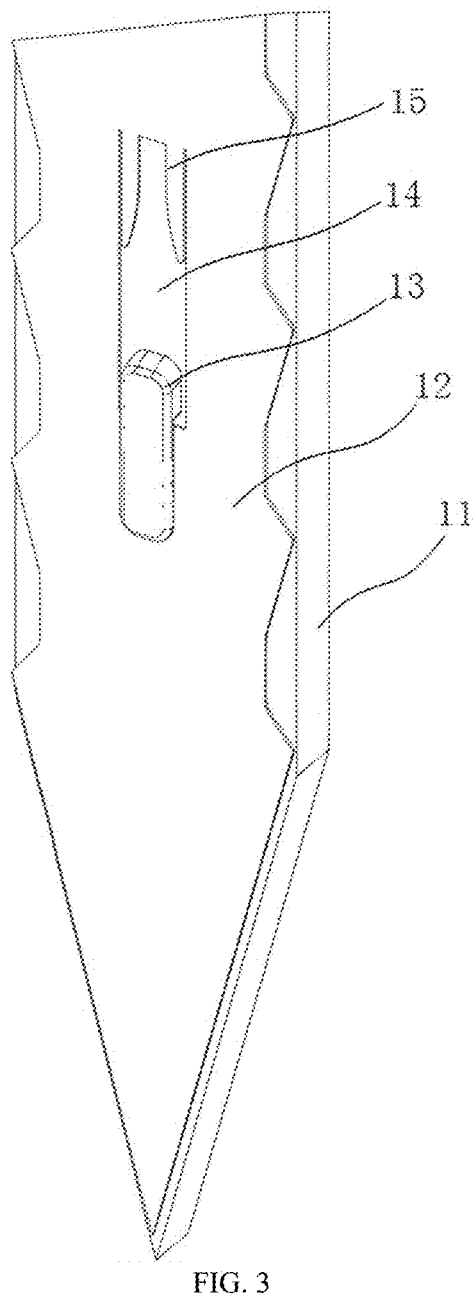
FIG. 3 is a schematic view of a fixed structure of a hard needle microelectrode and a soft needle microelectrode in a composite microneedle structure of the present application.
Figure 6:
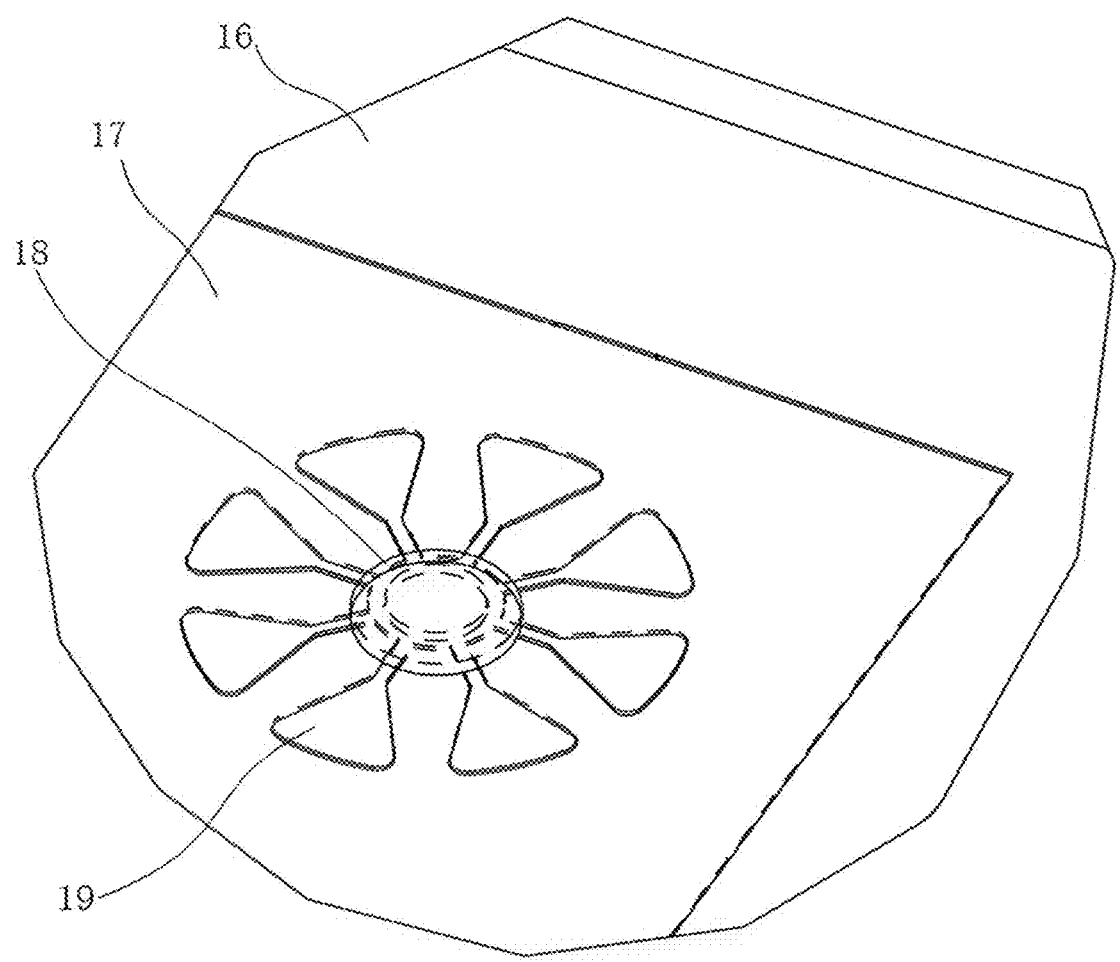
FIG. 6 is a schematic view of a fixed structure of a hard needle tail and a soft needle tail in a composite microneedle structure of the present application.

In an embodiment, as shown in FIG. 2, FIG. 3 and FIG. 6, the hard needle 3 is provided with a hard needle tail 16 and at least one hard needle microelectrode 11 formed on the hard needle tail 16, and the soft needle 4 is provided with a soft needle tail 17 and at least one soft needle microelectrode 12 formed on the soft needle tail 17; the soft needle microelectrode 12 is fixed to the hard needle microelectrode 11 by a first fixing member 6, and the soft needle tail 17 is fixed to the hard needle tail 16 by a second fixing member 5. The first fixing member 6 and the second fixing member 5 together constitute the above-mentioned fixed structural member, which plays a role in fixing the hard needle 3 and the soft needle 4, ensuring that the soft needle 4 can be implanted into the tissue together with the hard needle 3, and that no displacement occurs between the hard needle 3 and the soft needle 4. The integrated circuit chip 2 is fitted and fixed with the soft needle tail 17 to form an electrical connection, thereby realizing real-time, rapid and accurate extraction and stimulation of nerve signals.

Figure 4:
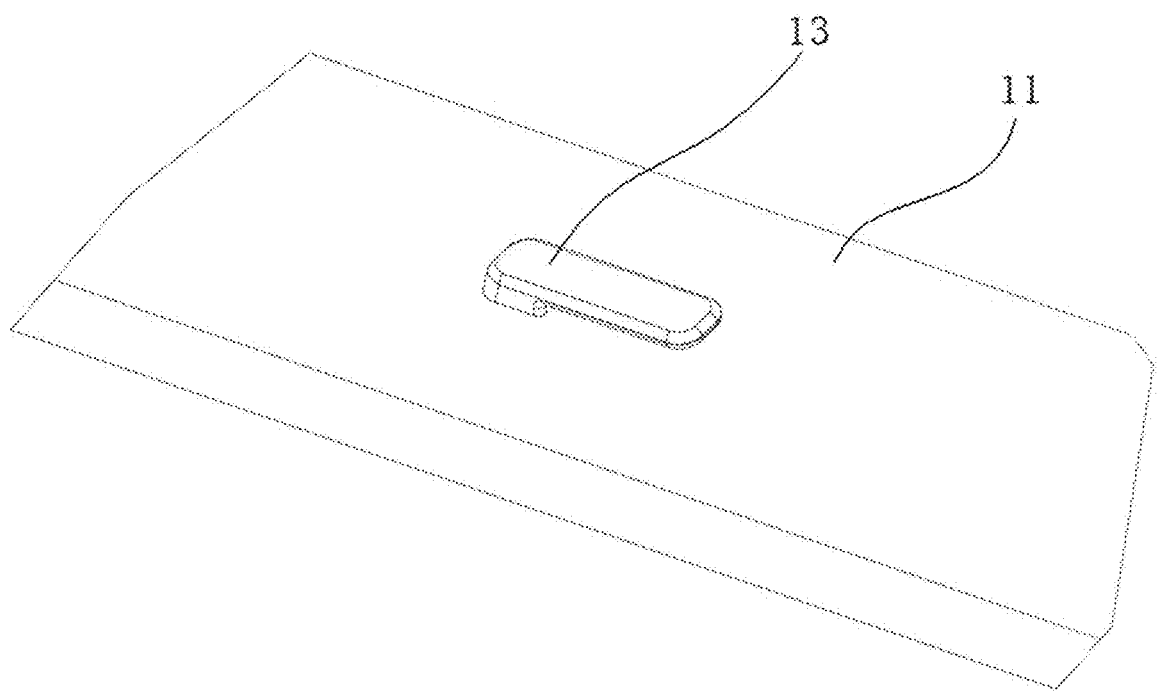
FIG. 4 is a structural schematic view of a hard needle microelectrode in a composite microneedle structure of the present application.
Figure 5:
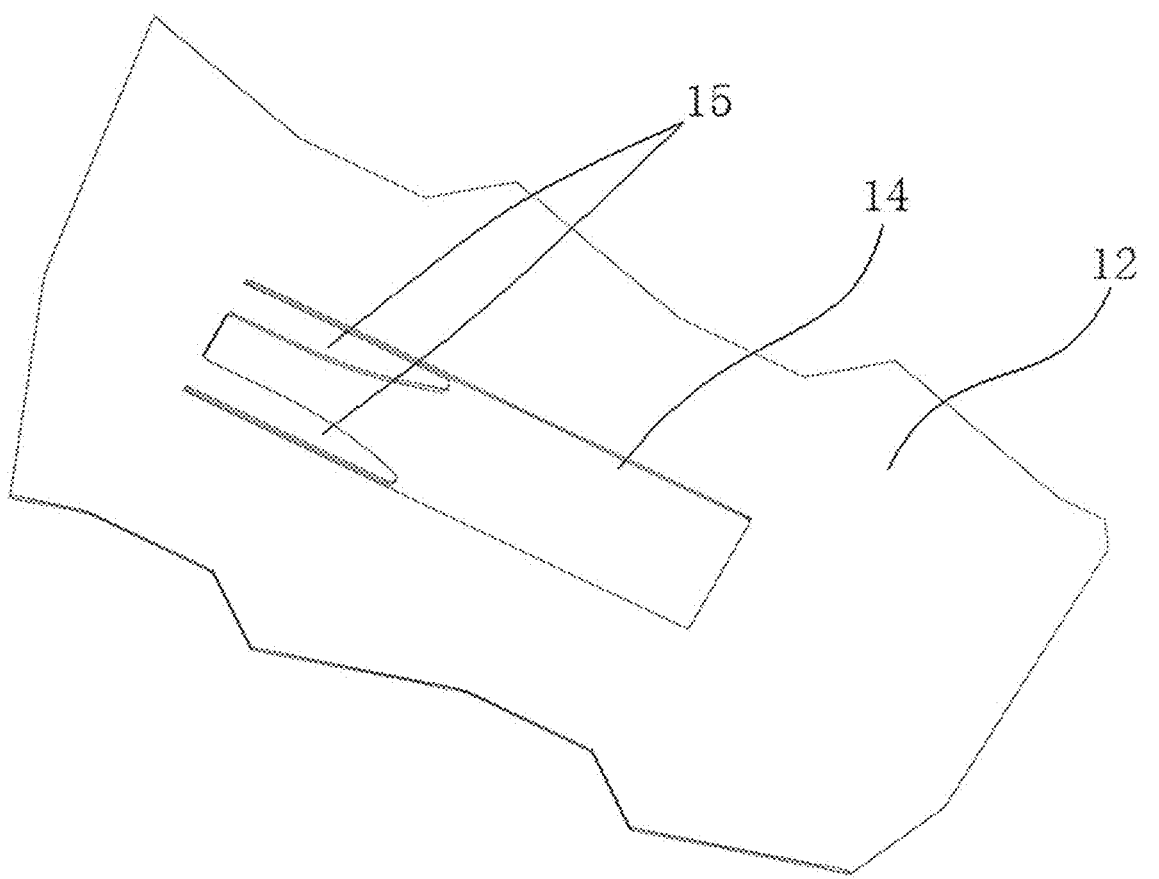
FIG. 5 is a structural schematic view of a soft needle microelectrode in a composite microneedle structure of the present application.

The specific structural design of the first fixing member 6 and the second fixing member 5 must not only satisfy the requirement of fixing the soft needle 4 when the microneedle is implanted into the tissue, so that the hard needle 3 can drive the soft needle 4 to be implanted into the tissue together, but also need to satisfy the requirement of conveniently separating the soft needle 4 from the hard needle 3 when the hard needle 3 is pulled out. Therefore, the optimized implementation scheme provides a specific structure of the first fixing member 6 and the second fixing member 5. As shown in FIG. 3, FIG. 4 and FIG. 5, the first fixing member 6 is a plurality of hook structures 13 provided at intervals along a length direction of the hard needle microelectrode 11, the hook structure 13 is provided with a first part and a second part, two ends of the second part are respectively connected to the first part and a surface of the hard needle microelectrode 11, and the first part is parallel to the surface of the hard needle microelectrode 11; the soft needle microelectrode 12 is provided between the first part and the surface of the hard needle microelectrode 11, and the second part and the surface of the hard needle microelectrode 11 are at a preset angle. Accordingly, an opening 14 for the hook structure 13 to pass through is provided at a position corresponding to the hook structure 13 on the soft needle microelectrode 12, and decoupling structures for the hook structure 13 to detach from the soft needle 4 is provided on the opening 14. Specifically, the first part of the hook structure 13, the second part of the hook structure 13 and the surface of the hard needle microelectrode 11 form an open slot facing a needle tip of the hard needle 3, and the decoupling structure is provided at one end away from a needle tip of the soft needle 4. When preparing the microprobe composed of the hard needle 3 and the soft needle 4, a sacrificial layer of a certain thickness is first grown on the surface of the hard needle 3, and then the soft needle 4 is grown on the surface of the sacrificial layer, an opening 14 is opened on the soft needle microelectrode 12 of the soft needle 4, a decoupling structure is patterned on the soft needle 4, then the second part of the hook structure 13 is grown at the opening 14, finally the first part of the hook structure 13 is grown, and then the sacrificial layer between the hard needle 3 and the soft needle 4 is released, so that the part of the soft needle microelectrode 12 at the edge of the opening 14 is pressed into the hook structure 13. When the hard needle 3 is implanted into the tissue, the hook structure 13 drives the soft needle 4 to be implanted together. After reaching the implantation site, the hard needle 3 is pulled backward. After the hook structure 13 on the hard needle microelectrode 11 contacts the decoupling structure at the rear end of the opening 14, the decoupling structure causes the hook structure 13 to separate from the soft needle microelectrode 12, and the fixation between the soft needle microelectrode 12 and the hard needle microelectrode 11 is released, thus achieving that the hard needle 3 is pulled out while the soft needle 4 remains in the tissue.

In an embodiment, as shown in FIG. 5, the decoupling structure is two decoupling parts 15 extending from an edge of the opening 14 into the opening 14, the two decoupling parts 15 are symmetrically provided about an axis of the opening 14; a spacing between the two decoupling parts 15 is smaller than a width of the second part of the hook structure 13, and a gap is provided between a side edge of the decoupling part 15 and a side edge of a corresponding opening 14, so that the decoupling parts 15 can be flipped up and squeezed in both directions. When the hard needle 3 is pulled out, the hard needle 3 is pulled backward, and after the hook structure 13 contacts the decoupling part 15, the decoupling part 15 will slowly tilt upward, so that the hook structure 13 will exit the opening 14 downward. For optimization, the two decoupling parts 15 and the soft needle microelectrode 12 can be designed as an integrally formed structure, so that during the process that the two decoupling parts 15 are opened upward, the second part of the hook structure 13 squeezes the decoupling part 15, so that the decoupling part 15 is tilted upward along the direction of the hard needle 3 retreating, thereby expanding the area of the opening 14, and the hook structure 13 is detached from the soft needle 4 from the opening 14. The soft needle 4 and the decoupling part 15 are made of elastic materials. After the hard needle 3 is detached from the soft needle 4, the tilted part of the decoupling part 15 drops and returns to its original shape.

In an embodiment, as shown in FIG. 3 to FIG. 5, in order to improve the strength of the hook structure 13, the first part of the hook structure 13 and the second part of the hook structure 13 are integrally formed. In the process of separating the hard needle 3 and the soft needle 4, in order to facilitate the hook structure 13 to detach from the opening 14, and to avoid the first part from affecting the decoupling part 15 during the process of the hook structure 13 squeezing the decoupling part 15, in this embodiment, the bottom surface of the second part is designed to abut against the surface of the hard needle microelectrode 11, the top surface of the second part abuts against the bottom surface of the first part, and the bottom surface of the second part is larger than the top surface of the second part.

In an embodiment, in order to facilitate the hard needle 3 to detach from the soft needle 4, in this embodiment, the preset angle between the second part of the hook structure 13 and the surface of the hard needle microelectrode 11 is set to an acute angle. That is, to avoid the first part exceeding the end of the second part in the direction away from the needle tip of the hard needle 3. At the same time, it is beneficial for the second part of the hook structure 13 to squeeze the decoupling part 15 and make the decoupling part 15 tilt upward.

Figure 7:
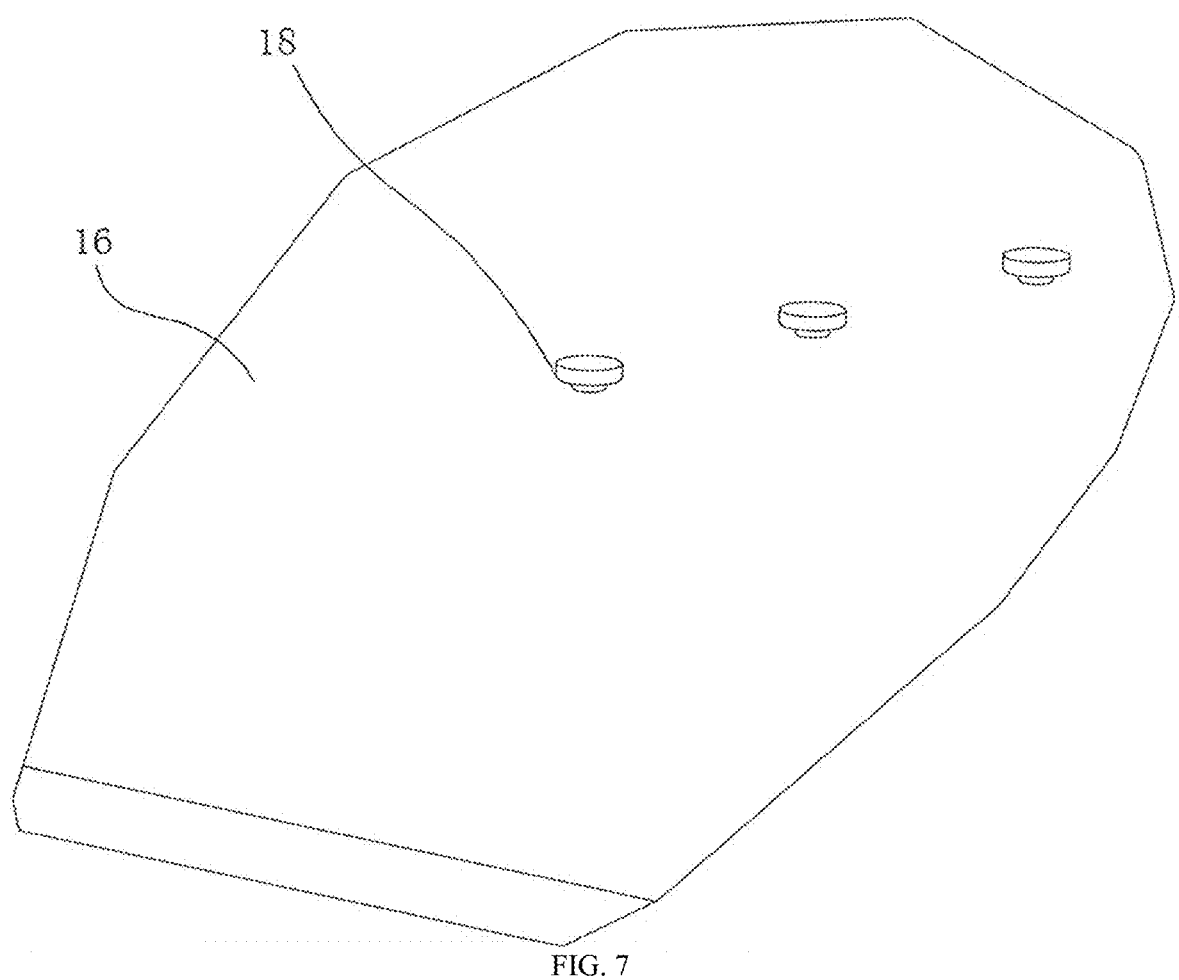
FIG. 7 is a structural schematic view of a hard needle tail in a composite microneedle structure of the present application.
Figure 8:
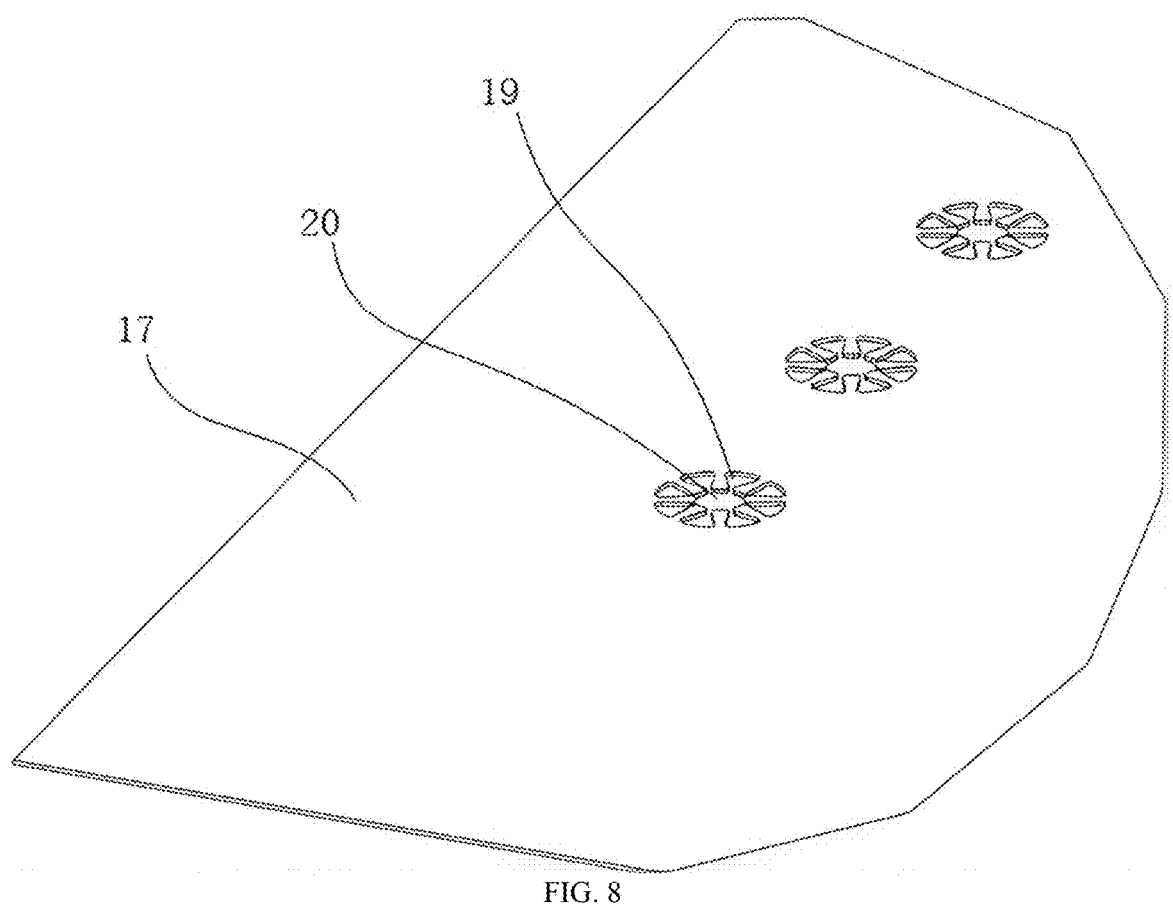
FIG. 8 is a structural schematic view of a soft needle tail in a composite microneedle structure of the present application.

For a specific structure of the second fixing member 5, as shown in FIG. 6, FIG. 7 and FIG. 8, the second fixing members 5 are a plurality of plug structures 18 provided at intervals along a width direction of the hard needle 3 at the hard needle tail 16, the plug structure 18 includes two coaxial cylinders with a larger upper part and a smaller lower part, a plug hole 20 is provided at the soft needle tail 17 corresponding to the plug structure 18, and a plurality of central symmetrical FIG. 19 are provided outward along an edge of the plug hole 20 on the soft needle tail 17, the central symmetrical FIG. 19 may be a petal-like structure as shown in the figure in this embodiment, and an upper cylinder diameter of the plug structure 18 is larger than a diameter of the plug hole 20. When fixing the hard needle 3 and the soft needle 4, the upper cylinder of the plug structure 18 passes through the corresponding plug hole 20 on the soft needle tail 17. Since the diameter of the upper cylinder of the plug structure 18 is larger than the diameter of the plug hole 20, the upper cylinder will press the part of the soft needle structure on the edge of the plug hole 20, thereby fixing the soft needle 4, and ensuring that no displacement occurs between the hard needle 3 and the soft needle 4. When the hard needle 3 drives the soft needle 4 to be implanted into the tissue together, by pulling the hard needle 3 downward, the upper cylinder of the plug structure 18 will exert a certain downward force on the soft needle 4, the central symmetrical FIG. 19 on the soft needle 4 will bend and deform to a certain extent until the plug structure 18 is completely withdrawn, and then the hard needle 3 is continued to be pulled backward to withdraw the hook structure 13 on the hard needle 3, thereby making the hard needle 3 and the soft needle 4 is completely detached, the hard needle 3 is pulled out, and the soft needle 4 is kept in the tissue.

In this embodiment, the center point of the central symmetrical FIG. 19 coincides with the center point of the plug hole 20.

In an embodiment, a connection between the soft needle tail 17 and the integrated circuit chip 2 is provided between the second fixing member 5 and the soft needle microelectrode 12. This structural design can effectively reduce the influence of the downward pulling force on the connection between the soft needle tail 17 and the integrated circuit chip 2 when the hard needle 3 is pulled down to separate the soft needle tail 17 from the hard needle tail 16, thereby ensuring the stability of the connection between the integrated circuit chip 2 and the soft needle 4.

Figure 9:
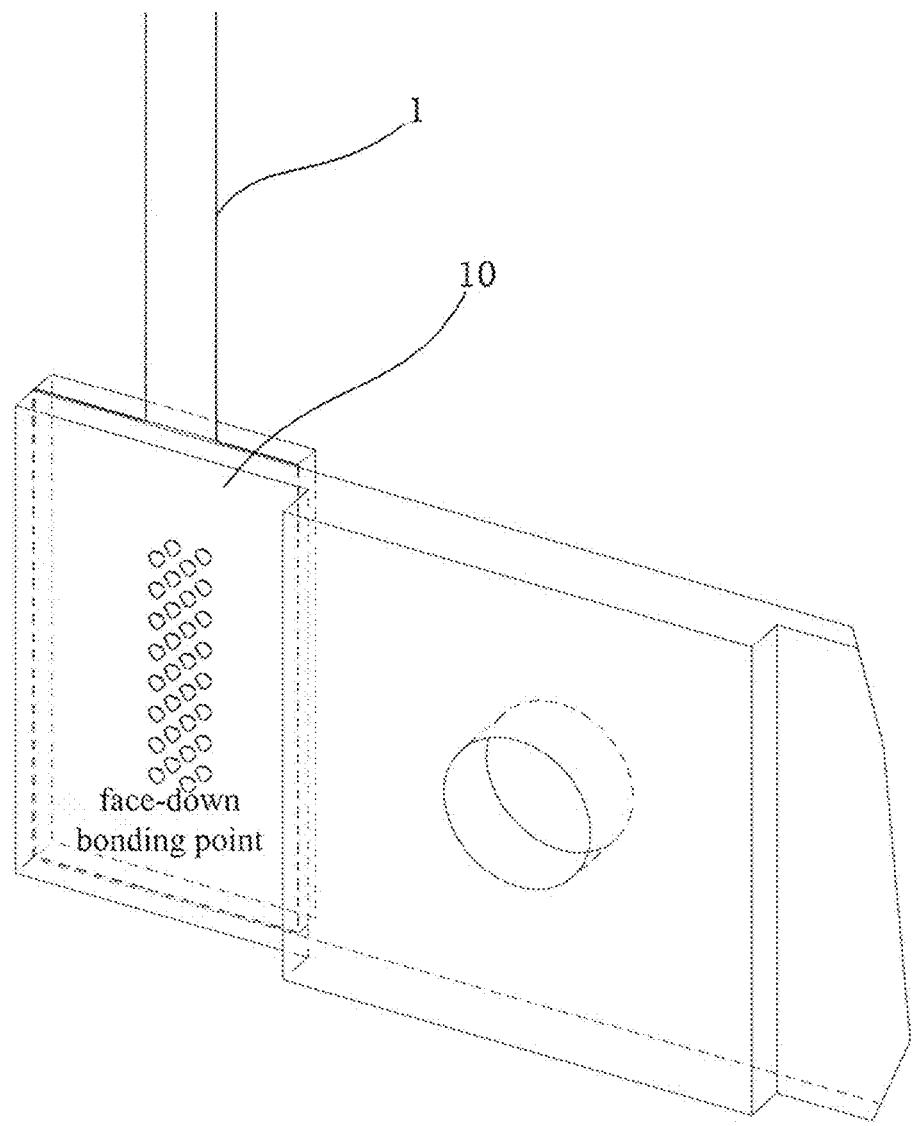
FIG. 9 is a schematic view of a connection between a microstrip line and an integrated circuit chip in the composite microneedle structure of the present application.
Figure 10:
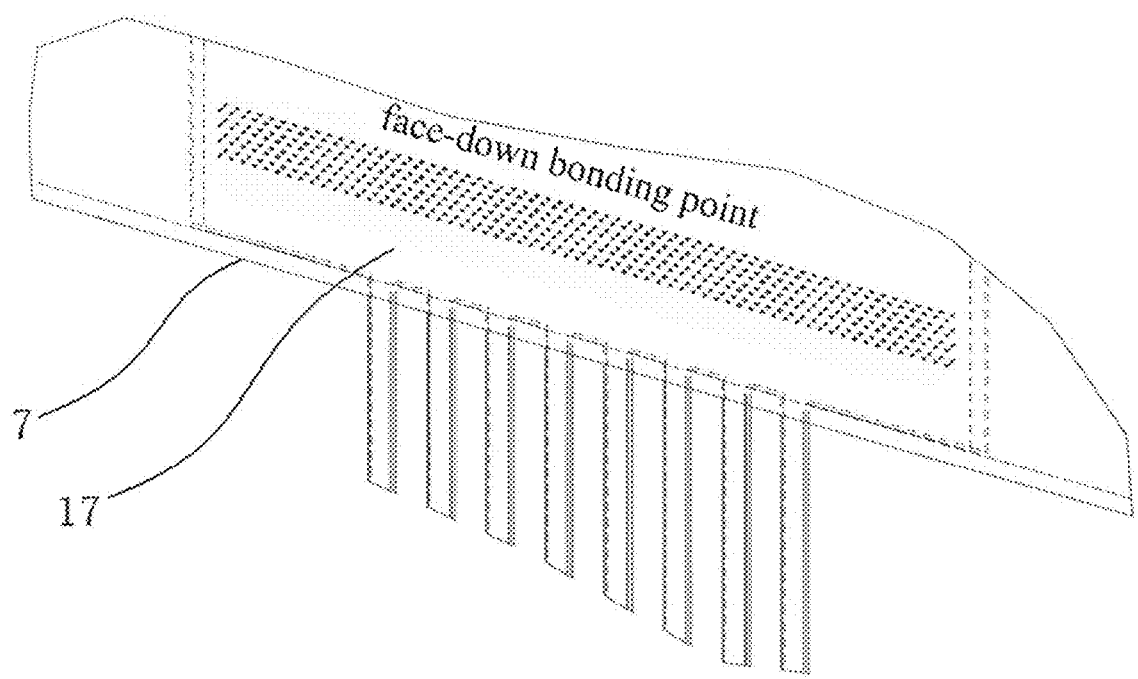
FIG. 10 is a schematic view of a connection between a microprobe and an integrated circuit chip in the composite microneedle structure of the present application.

In an embodiment, as shown in FIG. 1, FIG. 9 and FIG. 10, the integrated circuit chip 2 includes a soft needle connecting section 7 for connecting to the soft needle 4 and a microstrip line connecting section 10 for connecting to the microstrip line 1, and the microstrip line connecting section 10 is provided at one side of the soft needle connecting section 7. In an embodiment, the integrated circuit chip 2 is electrically connected to the soft needle 4 of the microprobe by face-down bonding, and the microstrip line 1 is electrically connected to the integrated circuit chip 2 by the face-down bonding. By directly face-down bonding the microprobe and the microstrip line 1 to the integrated circuit chip 2, thus achieving the real-time, fast and accurate extraction and stimulation of neural signals to minimize transmission loss and reduce noise signals, thereby ensuring stable and lossless signal transmission.

Furthermore, when multiple above-mentioned composite microneedle structures are provided, the integrated circuit chip 2 can also be designed to include a chip connecting section 8 for connecting with other integrated circuit chips 2. The chip connecting section 8 is located at both ends of the soft needle connecting section 7, and a connecting through hole 9 is provided on the chip connecting section 8. A single microprobe is connected to the integrated circuit chip 2 according to the connection method in the above embodiment. The connection between the multiple integrated circuit chips 2 can be fixed by connecting and fixing the connecting through holes 9 of each integrated circuit chip 2 by steel needle, so that the microprobe can be assembled into a planar array structure, thereby improving the application range of the composite microneedle structure.

In summary, the composite microneedle structure based on the integrated circuit chip provided by the present application can bring the soft needle into the tissue by the hard needle and then pull out the hard needle, which can not only fix the soft needle and the hard needle well to prevent them from moving, but also avoid the defects of using a single hard needle or a single soft needle. At the same time, the microprobe is integrated with the integrated circuit chip, which can realize the on-site collection and stimulation of neural signals, and accordingly optimize the functionality of the neural interface to better meet clinical needs.

The above examples are only examples of the present application and do not constitute a limitation on the scope of the present application. All designs that are the same or similar to the present application belong to the scope of the present application.

What is claimed is:

1. A composite microneedle structure based on an integrated circuit chip, comprising:
    a microstrip line;
    at least one microprobe; and
    at least one integrated circuit chip, wherein
    the microprobe comprises a hard needle and a soft needle, the soft needle is fixed to an upper surface of the hard needle by a fixed structural member, and the integrated circuit chip is provided at a tail of the microprobe; the integrated circuit chip and the soft needle of the microprobe are fixed to form an electrical connection, and the microstrip line and one end of the integrated circuit chip are fixed to form the electrical connection;
    the hard needle is provided with a hard needle tail and at least one hard needle microelectrode formed on the hard needle tail, and the soft needle is provided with a soft needle tail and at least one soft needle microelectrode formed on the soft needle tail; the soft needle tail is fixed to the hard needle tail, and the soft needle microelectrode is fixed to the hard needle microelectrode;
    the fixed structural member comprises a first fixing member for fixing the soft needle microelectrode and the hard needle microelectrode, and second fixing members for fixing the soft needle tail and the hard needle tail; and
    the second fixing members are a plurality of plug structures provided at intervals along a width direction of the hard needle at the hard needle tail, the plug structure comprises two coaxial cylinders with a larger upper part and a smaller lower part, a plug hole is provided at the soft needle tail corresponding to the plug structure, and a plurality of central symmetrical figures are provided outward along an edge of the plug hole on the soft needle tail, and an upper cylinder diameter of the plug structure is larger than a diameter of the plug hole.

2. The composite microneedle structure based on the integrated circuit chip according to claim 1, wherein the first fixing member is a plurality of hook structures provided at intervals along a length direction of the hard needle microelectrode, the hook structure is provided with a first part and a second part, two ends of the second part are respectively connected to the first part and a surface of the hard needle microelectrode, and the first part is parallel to the surface of the hard needle microelectrode; the soft needle microelectrode is provided between the first part and the surface of the hard needle microelectrode, and the second part and the surface of the hard needle microelectrode are at a preset angle.

3. The composite microneedle structure based on the integrated circuit chip according to claim 2, wherein the preset angle between the second part of the hook structure and the surface of the hard needle microelectrode is an acute angle.

4. The composite microneedle structure based on the integrated circuit chip according to claim 2, wherein an opening for the hook structure to pass through is provided at a position corresponding to the hook structure on the soft needle microelectrode, and decoupling structures for the hook structure to detach from the soft needle is provided on the opening; the first part of the hook structure, the second part of the hook structure and the surface of the hard needle microelectrode form an open slot facing a needle tip of the hard needle, and the decoupling structure is provided at one end away from a needle tip of the soft needle.

5. The composite microneedle structure based on the integrated circuit chip according to claim 4, wherein the decoupling structures comprise decoupling parts extending from an edge of the opening into the opening, a spacing between the decoupling parts is smaller than a width of the second part of the hook structure, and the decoupling parts are symmetrically provided about an axis of the opening; a gap is provided between a side edge of the decoupling parts and a side edge of a corresponding opening.

6. The composite microneedle structure based on the integrated circuit chip according to claim 1, wherein a connection between the soft needle tail and the integrated circuit chip is provided between the second fixing member and the soft needle microelectrode.

7. The composite microneedle structure based on the integrated circuit chip according to claim 1, wherein the integrated circuit chip comprises a soft needle connecting section for connecting to the soft needle and a microstrip line connecting section for connecting to the microstrip line, and the microstrip line connecting section is provided at one side of the soft needle connecting section; the integrated circuit chip is electrically connected to the soft needle of the microprobe by face-down bonding, and the microstrip line is electrically connected to the integrated circuit chip by the face-down bonding.

* * * * *